US006900342B2

(12) United States Patent  
Sharma et al.

(10) Patent No.: US 6,900,342 B2
(45) Date of Patent: May 31, 2005

(54) ANTICANCER TAXANES SUCH AS PACLITAXEL, DOCETAXEL AND THEIR STRUCTURAL ANALOGS, AND A METHOD FOR THE PREPARATION THEREOF

(75) Inventors: Arun Prakash Sharma, West Bengal (IN); Subrata Sarkar, West Bengal (IN); Jyan Shankar Mahanty, West Bengal (IN)

(73) Assignee: Dabur India Limited, Nadia (IN)

( * ) Notice: Subject to any disclaimer, the term of this patent is extended or adjusted under 35 U.S.C. 154(b) by 0 days.

(21) Appl. No.: 10/431,499

(22) Filed: May 8, 2003

(65) Prior Publication Data

US 2004/0073044 A1 Apr. 15, 2004

(30) Foreign Application Priority Data

May 17, 2002 (IN) .................................................. 294/02

(51) Int. Cl.$^7$ ............................................. C07D 493/00

(52) U.S. Cl. ...................................... 549/510; 549/511

(58) Field of Search ................................ 549/510, 511; 548/215

(56) References Cited

U.S. PATENT DOCUMENTS

| | | | |
|---|---|---|---|
| 4,924,011 A | 5/1990 | Denis et al. |
| 5,476,954 A | 12/1995 | Bourzat et al. |
| 5,616,739 A | 4/1997 | Mas et al. |
| 5,637,723 A | 6/1997 | Commercon et al. |
| 6,002,022 A | 12/1999 | Authelin et al. |
| 6,022,985 A | 2/2000 | Authelin et al. |
| 6,130,336 A | 10/2000 | Kim et al. |
| 6,197,980 B1 | 3/2001 | Durand et al. |
| 6,500,966 B1 | 12/2002 | Bombardelli |
| 6,506,905 B1 | 1/2003 | Prakash et al. |

OTHER PUBLICATIONS

Chen, Shu–Hui et al, Taxol structure–activity relationships: synthesis and biological evaluation of taxol analogs modified at C–7 CA 122:240034 (1995).*
Deprez, Dominique et al, "Process for the preparation of taxane derivatives" CA 120:333702 (1994).*
U.S. Appl. No. 10/430,433, filed May 7, 2003, Sharma et al.
U.S. Appl. No. 10/358,384, filed Feb. 5, 2003, Sharma et al.
U.S. Appl. No. 10/419,782, filed Apr. 22, 2003, Sharma et al.
U.S. Appl. No. 10/213,431, filed Aug. 7, 2002, Sharma et al.
Wani et al., J. Am. Chem. Soc., vol. 93, pp. 2325–2326 (1971).

* cited by examiner

*Primary Examiner*—Amelia A. Owens
(74) *Attorney, Agent, or Firm*—Venable LLP; Marina V. Schneller

(57) ABSTRACT

A process for the preparation of taxanes comprising

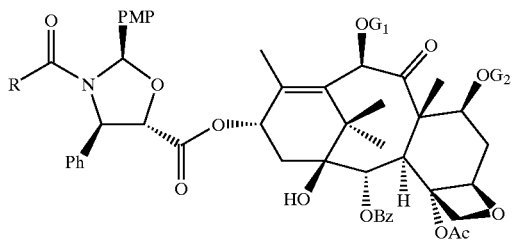

wherein R is a tert. butoxycarbonyl or benzoyl group; PMP is p-methoxyphenyl group; $G_1$ is acetyl group; $G_2$ is haloacetyl group comprising
  a) protecting the C-7 hydroxyl group of 10-deacetylbaccatin III with haloacetyl chlorides and then acetylating the C-10 hydroxyl group with acetyl chloride to obtain a protected 10-deacetylbaccatin III (1);
  b) subjecting the protected 10-deacetylbaccatin III (1) to coupling with an oxazolidine-5-caboxylic acid of formula 2

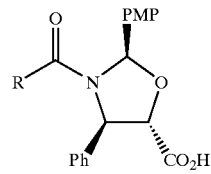

wherein R is tert. butoxycarbonyl or benzoyl; PMP is p-methoxyphenyl group in the presence of a condensation agent and an activating agent to obtain C-13 esters of formula 3;
  c) treating the coupled products 3 with weak acidic medium to open the oxazolidine ring to obtain intermediates of formula 4;

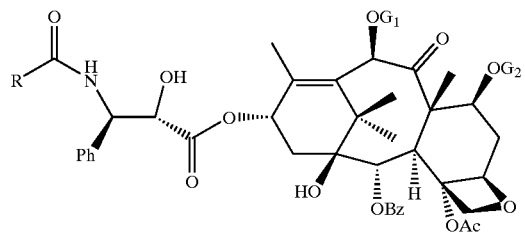

4a $G_1$ = acetyl; $G_2$ = 2-haloacyl; R = Ph
4b $G_1$ = $G_2$ = 2-haloacyl; R = t-butoxyl wherein R is a tert. butoxycarbonyl or benzoyl group; $G_1$ is acetyl group; $G_2$ is haloacetyl group
  d) subjecting the intermediates of compound 4 to selective deprotection of haloacyl group in the presence of acetyl group under mild alkaline condition at −20 to +40° C. for 6–24 h in the presence of ammonia or aliphatic amine or aromatic amines or their combination to obtain paclitaxel or docetaxel.

13 Claims, No Drawings

ANTICANCER TAXANES SUCH AS PACLITAXEL, DOCETAXEL AND THEIR STRUCTURAL ANALOGS, AND A METHOD FOR THE PREPARATION THEREOF

FIELD OF THE INVENTION

This invention relates to a process for the preparation of taxanes such as paclitaxel, docetaxel and their structural analogs. The taxanes are very important anticancer drugs.

BACKGROUND OF THE INVENTION

Paclitaxel is a diterpene taxane found in very low concentration in the bark of Pacific yew tree *Taxus brevifolia*. A number of semi-synthetic strategies have been developed for its synthesis from more readily available 10-DAB. However, the taxane nucleus is highly prone to degradation and semi-synthetic crude materials are often contaminated with structurally similar impurities. As a result, elaborate purification procedure using HPLC are required to produce pharmaceutical grade material. Thus, it becomes highly desirable to develop alternative routes, which involves minimal degradation.

In general, synthetic strategy for the semi-synthesis of paclitaxel/docetaxel comprises a) selective acylation/protection at similarly reactive C-7 and C-10 hydroxyl groups. Among the 1, 7, 10 and 13-hydroxyl groups in 10-DAB, the order of reactivity is 7>10>13>1. This requires selection of appropriate protecting groups, which can be put selectively and removed selectively under mild condition. Until recently, trialkylsilyl group, particularly triethylsilyl has been considered as the protecting group of choice for C-7 hydroxyl group. U.S. Pat. No. RE 34,277 (reissue of U.S. Pat. No. 4,924,011) describes conversion of 10-DAB into 7-triethylsilyl-10-deacetylbaccatin III, which is then acetylated at the 10-position with an acetylating agent. However, this process requires use of 5 to 20 equivalents of costly silylating agent and yields of each these steps were around 85% only. In U.S. Pat. No. 6,130,336, Kim et al., describes use of trichloroacetyl halides to protect C-7 hydroxyl group selectively followed by acetylation at 10-position with acetyl bromide. On the other hand, in U.S. Pat. No. 6,500,966 simultaneous protection of both C-7 and C-10 hydroxyl group is carried out with trichloroacetyl anhydride. Recently, we have explored the use of haloalkonyl as protecting groups (U.S. Provisional Patent Application. No 60/311,077). These haloalkonoyl groups undergo hydrolysis faster than unsubstituted alkonoyl groups and their deprotection causes minimum degradation. Also, these acid chlorides are cheaper and more easily available in comparison to trichloroacetyl halides used in U.S. Pat. No. 6,130,336 or trichloroacetic anhydride used in U.S. Pat. No. 6,500,966.

b) selective esterification of 13-hydroxyl group with a suitably protected N-benzoylphenylisoserine. It is known that esterification step proceeds to completion with cyclic forms of α-hydroxy-β-amidoarylcarboxylic acids such as oxazolidine carboxylic acid. Furthermore, when cyclic forms of C-13 side chain is used, no 2'-epimers is obtained as side product. Use of oxazolidine side chain generally requires protection of the 3-position of the side chain with a substituted carbonyl group as the amino group at 3-position tends to react with carboxylic acid group of another oxazolidine molecule thereby retarding the coupling reaction. It has been observed that nitrogen of oxazolidine ring does not require protection when 2-position is substituted with trihalomethyl or phenyl substituted with a trihalomethyl group. Oxazolidine carboxylic acid having two halomethyl substituents at 2-position and an unprotected nitrogen atom has been reported to undergo smooth coupling with a suitably protected 10-DAB (U.S. Pat. No. 6,130,336).

c) conversion of side chain precursor part into side chain and removal of the protecting groups from baccatin part. These reaction conditions should be mild in nature to afford final material in high yield with few side products.

Most of the nitrogen protecting groups used in oxazolidine carboxylic acid requires harsh acidic condition or hydrogenolysis for their removal and thus do not fulfil the criteria mentioned above. Also removal of nitrogen protecting group leads to an amine intermediate, which is not so stable and results in crude which are difficult to purify. Obviously it would be better if we could use benzoyl or tert. butoxycarbonyl group as the nitrogen protecting group in the oxazolidine side chain and open the oxazolidine ring under mild condition so that these groups are retained.

Thus, U.S. Pat. No. 5,637,723, issued to Rhone Poulenc Rorer S. A. in 1997, described an oxazolidine carboxylic acid, which incorporated benzoyl group as the nitrogen-protecting group. Consequently, the coupled product upon deprotection does not require to be benzoylated. An alternative approach has been described in U.S. Pat. No. 6,500,966, wherein a coupled product is first deprotected to remove the protecting trichloroacetyl groups on the deacetylbaccatin moiety followed by optional acetylation at C-10 hydroxyl group and subsequent acid hydrolysis of the oxazolidine ring.

Herein, the Applicants have described new intermediates for taxoid anti-cancer drugs, their process of synthesis and process for synthesis of paclitaxel and docetaxel using them in Scheme 1.

OBJECTS OF THE INVENTION

The object of this invention is to propose a novel process for the preparation of anticancer taxanes. Another object of the present invention is to propose a new process for the preparation of intermediates of taxanes.

Yet another object of this invention is to propose a process for preparation of paclitaxel, docetaxel and their analogues using intermediates, which minimize degradation during the process and thereby increase yield and purity of the target product.

Scheme-1

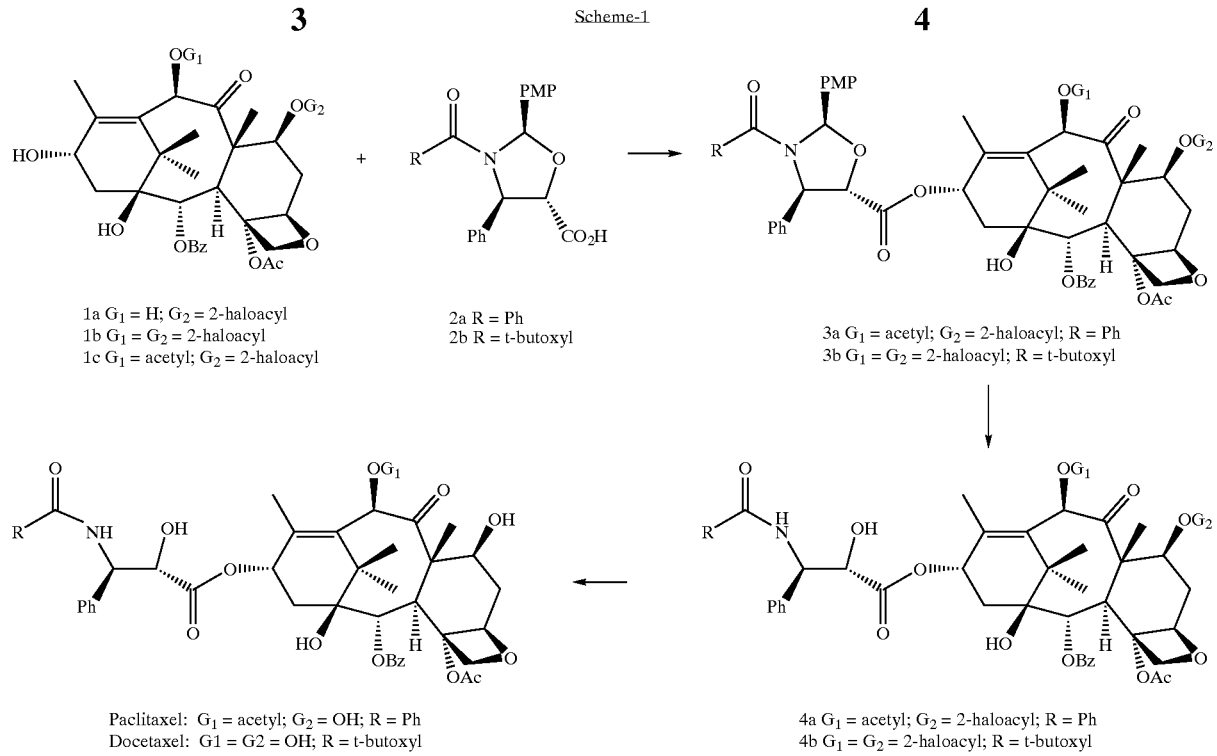

SUMMARY OF THE INVENTION

The present invention consists of a process for the preparation of taxanes comprising subjecting 7-O-(2-haloacyl) baccatin 1c to coupling with 5-oxazolidine carboxylic acid 2a or 7, 10-di-O-(2-haloacyl)-10-deacetylbaccatin 1b to coupling with 5-oxazolidine carboxylic acid 2b in the presence of a condensation agent and an activating agent in an aromatic hydrocarbon at a temperature between 25 and 100° C. to obtain coupled product 3a or 3b; treating the coupled products 3a and 3b with a weak acidic medium for deprotection in the side chain to afford the taxane intermediates 4a and 4b, respectively; followed by treatment of taxane precursors 4a and 4b with ammonia or aliphatic or aroatic amine or their combination at −20° to +40° C. for selective removal of 2-haloacyl group without any degradation of the taxane moiety to afford paclitaxel and docetaxel, respectively.

DETAILED DESCRIPTION OF THE INVENTION

The present invention provides a process for the preparation of taxanes and its analogs.

(4R,5S)-2-(p-Methoxyphenyl)-3-benzoyl-4-phenyl-1, 3-oxazolidine-5-carboxylic acid 2a is coupled with 7-O-(2-haloacyl)baccatin III 1c in the presence of a condensation agent and an activating agent in an aromatic hydrocarbon as solvent to obtain 7-O-[2-(chloroacetyl)]-13-[(4S,5R)-2-(p-methoxyphenyl)-3-benzoyl-4-phenyl-1, 3-oxazolidinyl-5-carbonyl]baccatin III (3a). Among condensation agents used dicyclohexylcarbodiimide is found to be preferable, while 4-dimethylaminopyridine is found to be preferable as an activating agent.

The reaction is carried out at temperature between 0–100° C., more preferably at 40–80° C., most preferably at 60° C. Among aromatic hydrocarbons, toluene is found most suitable.

Similarly 7, 10-di-O-chloroacetyl-10-deacetylbaccatin III (1b) underwent smooth coupling with (4R, 5S)-2-(p-methoxyphenyl)-3-tert. butoxycarbonyl-4-phenyl-1, 3-oxazolidine-5-carboxylic acid 2b to provide the coupling product namely 7, 10-di-O-[2-(chloroacetyl)]-13-[(4S, 5R)-2(-p-methoxyphenyl)-3-tert. butoxycarbonyl-4-phenyl-1, 3-oxazolidinyl-5-carbonyl]-10-deacetylbaccatin III (3b). The condition used in this reaction is the same as described above for compound 3a.

(4R, 5S)-2-p-Methoxyphenyl)-3-benzoyltert. butoxycarbonyl-4-phenyl-1, 3-oxazolidine-5-carboxylic acid 2 can be prepared by condensing 4-methoxybenzaldehyde or 4-methoxybenzaldehyde dimethyl acetal with an isoserine ester. These oxazolidine carboxylic acids have also been used by Bombardelli et al (U.S. Pat. No. 6,500,966) who prepared them by known literature procedure and found them to be easily crystallisable and adjustable to 95:5 isomer ratio.

Opening of the oxazolidine ring in the coupled product 3 while retaining the nitrogen protecting group has to be achieved under mild condition so as to avoid degradation of taxane ring. We employed weak acidic condition by using a mixture of trifluoroacetic acid, acetic acid and water. The reaction is carried out at temperature between 20–40° C., preferably at 25–30° C. under stirring for 4–12 h, preferably for 6–8 h. The products obtained 4 were found to retain the nitrogen protecting benzoyl group or tert. butoxycarbonyl group.

The intermediate 4, under mild alkaline condition, in the presence of ammonia or aliphatic amines or aromatic amines or their combination, preferably ammonia and pyridine (1:5) undergoes selective deprotection of haloacyl groups without affecting the acetyl group at 10-position. The reaction is carried out at 0–5° C., preferably at 2° C. under stirring for 6–24 h, preferably 10 h to obtain paclitaxel or docetaxel.

In U.S. Pat. No. 6,500,966 to Bombardelli et al., deprotection of 7- and 10-trichloroacetyl group is carried out by using ammonium hydroxide/ammonium chloride in an aliphatic alcohol, preferably methanol. In our experience, taxane moiety is prone to degradation even under weak basic or acidic condition in protic solvents including alcohols and as a result crude produced are contaminated with degradation products which are difficult to remove.

In the process of invention, selective removal of protecting monohaloacetyl group at 7-hydroxyl group in the presence of an acetyl group at 10-hydroxyl has been achieved under much milder condition. Furthermore, the procedure described by U.S. Pat. No. 6,500,966 requires three steps to convert the coupling product to paclitaxel, whereas this invention describes a two step strategy.

The process developed by Kim et al. (U.S. Pat. No. 6,130,336) also requires three steps to convert coupling product into paclitaxel and involves isolation of an amine, which as pointed out earlier, are not so stable intermediate and are prone to degradation.

The invention will now be explained in greater details with the help of following examples:

Experimental

Synthesis of 7-O-chloroacetyl-10-deacetylbaccatin III (1a)

A mixture of 10-deacetylbaccatin III (250 gm, 0.46 mole), pyridine (150 gm) and 4-DMAP (5.6 gm, 46 mmol) is dissolved in dichloromethane (2.0 L). The reaction mixture is stirred for 10 minutes. Chloroacetylchloride (75 gm, 0.66 mole) dissolved in dichloromethane (1.5L) is then slowly added to the reaction mixture at 25–30° C. The whole mixture is stirred for 20 minutes and then excess reagent is decomposed by adding 100 gm ice water, and acidified with 5% hydrochloric acid. The organic layer thus obtained is successively washed with aqueous sodium bicarbonate, sodium chloride solution, dried over anhydrous sodium sulfate, and then distilled under reduced pressure. The residue is dissolved in toluene (1.5L) at 70–80° C. and then cooled down to 0–5° C. The resulting fine solid is filtered and then washed with 1000 ml of hexane to obtain the pure title compound 1a (250 gm, 0.40 mole, yield 87%).

Synthesis of 7-O-chloroacetylbaccatin III (1c)

7-O-Chloroacetyl-10-deacetylbaccatin III (250 gm, 0.40 mole) is dissolved in pyridine (2.5L). The reaction mixture is cooled to 0–5° C. 190 gm (2.42 mole) of acetyl chloride is slowly added to the reaction mixture at 0–5° C. over a period of 40–50 min. Then the resulting mixture is further stirred 0–5° C. for 3 h. The excess reagent is decomposed by adding 200 ml water maintaining internal temperature 0–5° C. The solvent is then removed under reduced pressure and the residual mass is extracted with 2.5L of ethyl acetate. The organic layer thus obtained is washed with aqueous hydrochloric acid, sodiumbicarbonate and sodium chloride solution. The organic layer is evaporated under reduced pressure. The residue is dissolved in toluene(1.5 L) at 70–80° C. and then cooled down to 0° C. The resulting fine solid is filtered and then washed with 800 ml of hexane to obtain the pure title compound 1c (249.1 gm, 0.376 mole, yield 94%).

Synthesis of 7, 10-di-O-chloroacetyl-10-deacetylbaccatin III (1b)

A mixture of 10-deacetylbaccatin III (250 gm, 0.46 mole), pyridine (300 gm) and 4-DMAP (11.2 gm, 92 mmol) is dissolved in 2.0L of dichloromethane. The reaction mixture is stirred for 10 minutes. 150 gm (1.33 mole) of chloroacetyl chloride dissolved in 1.5 L dichloromethane is slowly added to the reaction mixture at 25–30° C. Then, the whole mixture is stirred for 20 minutes. 150 gm Ice water is added to decompose the excess reagent, and then the reaction mixture is acidified with 5% hydrochloric acid. The organic layer thus obtained is successively washed with aqueous sodiumbicarbonate, sodium chloride solution, dried over anhydrous sodium sulfate, and then distilled under reduced pressure. The residue is dissolved in toluene (1.5 L) at 70–80° C. and then cooled down to 0–5° C. The resulting fine solid is filtered and then washed with 1000 ml of hexane to obtain of the pure title compound 1b (304.6 gm, 0.437 mole, yield 95%).

7-O-[2-(Chloroacetyl)]-13-[(4S, 5R)-2-p-methoxyphenyl)-3-benzoyl-4-phenyl-1, 3-oxazolidinyl-5-carbonyl]baccatin III (3a)

A mixture of 7-O-(2-chloroacetyl)baccatin III (1c, 100 gm, 0.15 mole), (4S, 5R)-2(-p-methoxyphenyl)-3-benzoyl-4-phenyl-1, 3-oxazolidine-5-carboxylic acid (2a, 64.5 gm, 0.16 mole) and 4-dimethylaminopyridine (5.0 gm, 40.9 mmol) is dissolved in toluene (0.8 L) under nitrogen atmosphere. The temperature of the reaction mixture is raised to 50° C. under stirring and then a solution of DCC (45 gm, 0.22 mole) in toluene (0.2 L) is added to it. Exotherm occurs and the temperature of the reaction mixture automatically rises to 60° C. and that temperature is maintained for 30 minutes. The reaction mixture is then cooled to 25–30° C., diluted with ethyl acetate (2.5 L) and kept under stirring for 15 minutes. The reaction mixture is then filtered under suction. The residue is extracted with ethyl acetate (2×1.0 L). The combined organic layer is washed successively with 25% ammonium chloride solution, 5% aqueous sodium bicarbonate, water, and brine and then dried over anhydrous sodium sulfate. Evaporation of the organic layer under reduced pressure affords the crude product, which is then precipitated with DCM/Hexane (1:10) to obtain compound 3a (151 gm, 0.144 mole, 96%).

7, 10-Di-O-[2-(Chloroacetyl)]-13-[(4S, 5R)-2(-p-methoxyphenyl)-3-tert. butoxycarbonyl-4-phenyl-1, 3-oxazolidinyl-5-carbonyl]-10-deacetylbaccatin III (3b)

The compound 3b is obtained from 7, 10-di-O-(2-chloroacetyl)-10-deacetylbaccatin III (1b, 100 gm, 0.143 mole), (4S, 5R)-2-(p-methoxyphenyl)-3-tert. butoxycarbonyl-4-phenyl-1, 3-oxazolidine-5-carboxylic acid (2b, 61 gm, 0.153 mole) and 4-dimethylaminopyridine (4.80 gm, 39.29 mmol) and DCC (43.5 gm, 0.211 mole) in toluene (1.0 L) by following the protocol described above for the compound 3a.

Yield: 146.5 gm, 0.136 mole, 95%).

7-O-(2-Chlroacetyl)paclitaxel (4a)

7-O-[2-(Chloroacetyl)]-13-[(4S, 5R)-2-p-methoxyphenyl)-3-benzoyl-4-phenyl-1, 3-oxazolidinyl-5-carbonyl]baccatin III (3a, 105 gm, 0.1 mole) is added to a mixture of trifluoroacetic acid (95 ml), acetic acid (1050 ml) and water (105 ml). The mixture is stirred at 25–30° C. for 8 h and then poured into a solution of disodium hydrogen phosphate (2.5 KG in 5.0 L water) at 25–30° C. followed by dichloromethane (2.0 L). After extraction the organic layer is successively washed with saturated sodium bicarbonate, brine and then dried over anhyrous sodium sulfate. The solvent is evaporated under reduced pressure and the residue is subjected to column chromatography (eluent: ethylacetate/hexane, 2/5, v/v) to obtain the title compound 4a (84 gm, 0.090 mole, 90%).

7, 10-Di-O-(2-chlroacetyl)docetaxel (4b)

7, 10-Di-O-[2-(Chloroacetyl)]-13-[(4S, 5R)-2-(p-methoxyphenyl)-3-tert-butoxycabonyl-4-phenyl-1,3-oxazolidinyl-5-carbonyl]-10-deacetylbaccatin III (3b, 108 gm, 0.1 mole) is added to a mixture of trifluoroacetic acid (98 ml), acetic acid (1080 ml) and water (108 ml). The mixture is stirred at 25–30° C. for 8 h and then poured into a solution of disodium hydrogen phosphate (2.5 KG in 5.0 L water) at 25–30° C. followed by dichloromethane (2.0 L). After extraction the organic layer is successively washed with saturated sodium bicarbonate, brine and then dried over anhyrous sodium sulfate. Evaporation of the organic layer under reduced pressure followed by column chromatography (eluent: ethylacetate/hexane, 2/5, v/v) affords the compound 4b (82 gin, 0.085 mole, 85%).

Paclitaxel

To a pre-cooled solution (0–5° C.) of 25% ammonia (160 ml) in pyridine (800 ml) is added 7-O-(2-chloroacetyl) paclitaxel (4a, 80 gm, 85.98 mmol) and then stirred at this temperature for 12 h. The reaction is monitored by TLC. After the reaction is over, ammonia and pyridine is removed under low pressure. The resultant gum is dissolved in ethyl acetate (1.5L). The organic layer is washed successively with 2% hydrochloric acid, 5% sodium bicarbonate solution, and brine and then stored over anhydrous sodium sulfate. Evaporation of the organic layer under reduced pressure affords crude paclitaxel. The latter is on column chromatography on silica 60 with ethyl acetate/hexane (6/4) affords paclitaxel (63.1 gm, 73.89 mmol, 85.9%) as a white solid.

Docetaxel

Docetaxel is obtained from 7, 10-O-(2-chloroacetyl) docetaxel (9b, 80 gm, 83.26 mmol) using 25% ammonia (320 ml) in pyridine (1600 ml) and by following the protocol described above for paclitaxel. After column chromatography on silica 60 with ethyl acetate/hexane (6/4) docetaxel is obtained as a white solid. Yield: 56.5 gm, 69.93 mmol, 84%.

We claim:

1. A process for the preparation of taxanes comprising
   wherein R is a tert. butoxycarbonyl or benzoyl group; PMP is p-methoxyphenyl group; $G_1$ is acetyl group; $G_2$ is haloacetyl group comprising
   a) protecting the C-7 hydroxyl group of 10-deacetylbaccatin III with haloacetyl chlorides and then acetylating the C-10 hydroxyl group with acetyl chloride to obtain a protected 10-deacetylbaccatin III (1);
   b) subjecting the protected 10-deacetylbaccatin III (1) to coupling with an oxazolidine-5-caboxylic acid of formula 2
   wherein R is tert. butoxycarbonyl or benzoyl; PMP is p-methoxyphenyl group in the presence of a condensation agent and an activating agent to obtain C-13 esters of formula 3;
   c) treating the coupled products 3 with weak acidic medium to open the oxazolidine ring to obtain intermediates of formula 4;

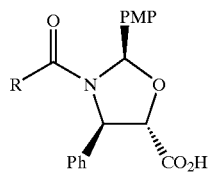

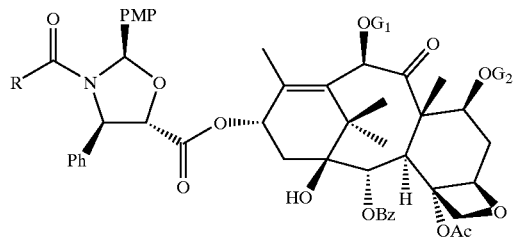

wherein R is a tert. butoxycarbonyl or benzoyl group; $G_1$ is acetyl group; $G_2$ is haloacetyl group; and
   d) subjecting the intermediates of compound 4 to selective deprotection of haloacyl group in the presence of acetyl group under mild alkaline condition at −20 to +40° C. for 6–24 h in the presence of ammonia or aliphatic amine or aromatic amines or their combination to obtain paclitaxel or docetaxel.

2. A process for preparing a compound of formula 3

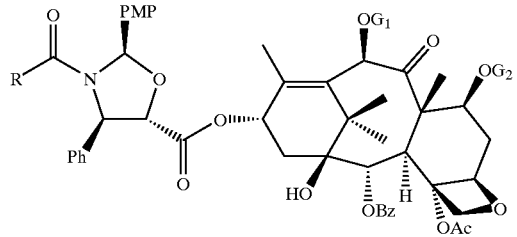

wherein R is a tert. butoxycarbonyl or benzoyl group; PMP is p-methoxyphenyl group; $G_1$ is acetyl group; $G_2$ is haloacetyl group comprising
   a) protecting the C-7 hydroxyl group of 10-deacetylbaccatin III with haloacetyl chlorides and then acetylating the C-10 hydroxyl group with acetyl chloride to obtain a protected 10-deacetylbaccatin III (1);
   b) subjecting the protected 10-deacetylbaccatin III (1) to coupling with an oxazolidine-5-caboxylic acid of formula 2

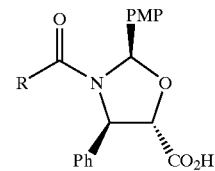

wherein R is a tert. butoxycarbonyl or benzoyl group; PMP is p-methoxyphenyl group in the presence of a condensation agent and an activating agent to obtain C-13 esters of formula 3.

3. A process as claimed in claim 1, wherein the said condensation agent used in step b) is preferably dicyclohexylcarbodiimide and the activating agent is preferably aminopyridine is preferably 4-dimethylaminopyridine.

4. A process as claimed in claim 1, wherein the said aromatic hydrocarbon used in step b) is preferably toluene.

5. A process as claimed in claim 1, wherein the reaction in step b) is carried out at temperature between 0–100° C. and preferably at 40–80° C., most preferably at 60° C.

6. The process of claim 1, wherein in step c) the acidic medium used is a mixture of trifluoroacetic acid, acetic acid and water.

7. The process of claim 1, wherein in step c) the process is carried out at 20–40° C. under stirring for 4–12 h.

8. The process of claim 1, wherein in step c) the process is most preferably carried out at 25–30° under stirring for 6–8 h.

9. The process of claim 1, wherein in step d selective deprotection of haloacetyl group in the presence of acetyl group in the intermediate of compound 4 is done by treating them with ammonia and pyridine at 0–5° C. for 6–24 h.

10. The process as claimed in claim 9 is most preferably carried out with a 1:5 mixture of ammonia and pyridine, at 2° C. for 10 h.

11. The intermediate compound 3 of formula

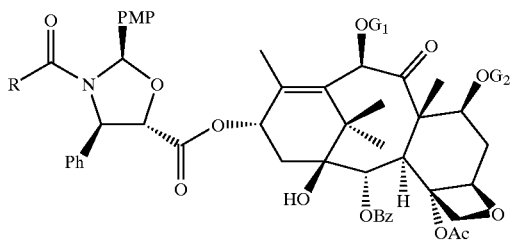

wherein R is a tert. butoxycarbonyl or benzoyl group; PMP is p-methoxyphenyl group; $G_1$ is acetyl group; $G_2$ is haloacetyl group.

12. The compound 3a as claimed in claim 11, wherein the compound is 7-O-[2-(chloroacetyl)]-13-[(4S, 5R)-2-(p-methoxyphenyl)-3-benzoyl-4-phenyl-1, 3-oxazolidinyl-5-carbonyl]baccatin III.

13. The compound 3b as claimed in claim 11, wherein the compound is 7-O-[2-(chloroacetyl)]-13-[(4S, 5R)-2-(p-methoxyphenyl)-3-tert. butoxycarbonyl-4-phenyl-1, 3-oxazolidinyl-5-carbonyl]baccatin III.

* * * * *